United States Patent [19]
Dudley

[11] Patent Number: 5,880,120
[45] Date of Patent: Mar. 9, 1999

[54] TREATING DEPRESSION BY ADMINISTERING AN ANTIDEPRESSANT

[75] Inventor: Mark W. Dudley, Hamilton, Ohio

[73] Assignee: Merrell Pharmaceuticals, Inc., Cincinnati, Ohio

[21] Appl. No.: 937,224

[22] Filed: Sep. 11, 1997

Related U.S. Application Data

[63] Continuation of Ser. No. 733,901, Oct. 18, 1996, abandoned, and a continuation of Ser. No. 440,511, May 12, 1995, abandoned, which is a continuation of Ser. No. 294,774, Aug. 23, 1994, abandoned, which is a continuation of Ser. No. 133,829, Oct. 7, 1993, abandoned, which is a continuation of Ser. No. 979,357, Nov. 20, 1992, abandoned, which is a continuation of Ser. No. 855,125, Mar. 18, 1992, abandoned, which is a continuation of Ser. No. 762,050, Sep. 18, 1991, abandoned, which is a continuation of Ser. No. 296,474, Jan. 12, 1989, abandoned, which is a division of Ser. No. 287,517, Dec. 19, 1988, abandoned, which is a continuation of Ser. No. 85,665, Aug. 14, 1987, abandoned.

[51] Int. Cl.$^6$ .................... A61K 31/55; A61K 31/135
[52] U.S. Cl. .................... 514/271; 514/651; 514/255; 514/277; 514/646; 514/469; 514/654; 514/656; 514/659
[58] Field of Search .................. 514/217, 255, 514/277, 646, 469, 654, 656, 659, 651

[56] References Cited

U.S. PATENT DOCUMENTS

| | | |
|---|---|---|
| 3,538,224 | 11/1970 | Nelson . |
| 3,883,537 | 5/1975 | Schroter ............................ 564/387 X |
| 3,890,330 | 6/1975 | Werner ............................... 564/378 |
| 4,062,840 | 12/1977 | Burg ................................. 564/387 X |
| 4,177,292 | 12/1979 | Nedelee et al. ................. 564/428 X |
| 4,254,056 | 3/1981 | Konno et al. ......................... 564/387 |
| 4,314,081 | 2/1982 | Molloy et al. ....................... 564/347 |
| 4,755,534 | 7/1988 | Stuetz ............................... 564/387 X |
| 5,149,714 | 9/1992 | Freedman ............................ 514/655 |

FOREIGN PATENT DOCUMENTS

| | | |
|---|---|---|
| 1067659 | 5/1967 | Br. Indian Ocean Ter. . |
| 96838 | 12/1983 | European Pat. Off. . |
| 0207600 | 1/1987 | European Pat. Off. . |
| 1792679 | 2/1972 | Germany . |
| 2091250 | 7/1982 | United Kingdom ......... C07D 212/12 |

OTHER PUBLICATIONS

The Merck Index (10$^{th}$ Ed.), Windholz et al., (1983), Nos. 2886 and 9394 on pp. 421 and 1370.

Physician's Desk Reference (44$^{th}$ Ed.), Henwood et al., pp. 905–906 and 1471 (1990).

N. Brunello et al. [Neuropharmacol. 21, 1145 (1982) ].

Janowsky et al. [Science 218, 900 (1982) ].

F. Sulser et al. [Ann. N.Y. Acad. Sci. 430, 91 (1984) ].

E. Mutschler in "Arzneimittelwirkungen", 5th ed., 1986, pp. 133–141.

Helwig and Helwig, "Moderne Arzneimittel", 5th ed., Wissenschaftliche Verlagsgesellschaft MBH, Stuttgart, 1980, pp. 163–232.

Wolfe, "Burger's Medicinal Chemistry", Part III, 4$^{th}$ Ed. pp. 1014–1015 and 1047 (1979).

Green, Theordora, W. Protective Groups in Organic Synthesis, A Wiley–Interscience Publication, John Wiley and Sons (1981), pp. 109–110.

*Primary Examiner*—Maruanne M. Cintins
*Assistant Examiner*—M. Moezie
*Attorney, Agent, or Firm*—Barbara E. Kurys

[57] ABSTRACT

The present invention provides novel compounds such as certain aryloxy indanamines which are useful as antidepressants and as inhibitors of synaptic norepinephrine and serotonin uptake. The present invention also provides an improvement in the treatment of depression which comprises inhibiting synaptic serotonin and epinepherine uptake.

1 Claim, No Drawings

TREATING DEPRESSION BY ADMINISTERING AN ANTIDEPRESSANT

CROSS-REFERENCE TO RELATED APPLICATION

This is a continuation of application Ser. No. 08/733,901, filed Oct. 18, 1996, now abandoned; which is a continuation of application Ser. No. 08/440,511, filed May 12, 1995, now abandoned; which is a continuation of application Ser. No. 08/294,774, filed Aug. 23, 1994, now abandoned; which is a continuation of application Ser. No. 08/133,829, filed Oct. 7, 1993, now abandoned; which is a continuation of application Ser. No. 07/979,357, filed Nov. 20, 1992, now abandoned; which is a continuation of application Ser. No. 07/855,125, filed Mar. 18, 1992, now abandoned; which is a continuation of application Ser. No. 07/762,050, filed Sep. 18, 1991, now abandoned; which is a continuation of application Ser. No. 07/296,474, filed Jan. 12, 1989, now abandoned; which is a divisional of application Ser. No. 07/287,517, filed Dec. 19, 1988 now abandoned; which is a continuation of application Ser. No. 07/085,665, filed Aug. 14, 1987, now abandoned, which is herein incorporated by reference.

The present invention provides novel compounds of the formula (1)

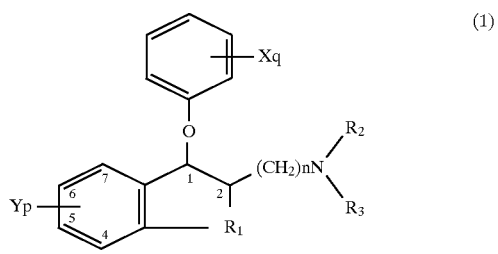

wherein
 $R_1$ is a $C_1$–$C_3$ alkylene,
 n, p and q are each independently 0, 1 or 2,
 Y and X are each independently lower alkyl, lower alkoxy, hydroxy, $CF_3$, halogeno or when p or q are 2 and each of the Y or each of the X groups are on adjacent aryl carbon atoms, both of the X or both of the Y groups can be taken together to form a methylenedioxy moiety,
 $R_2$ and $R_3$ are each independently hydrogen, lower alkyl, aralkyl, or $R_2$ and $R_3$ taken together with the nitrogen to which they are attached are pyrrolidino, mnorpholino, piperidino, piptrazino, or 4-methylpiperazino,
or an acid addition salt thereof.

$R_1$ is a divalent alkylene group comprised of 1 to 3 carbon atoms of straight or branched chain configuration including, for example, —$CH_2$—, —$CH_2CH_2$—, —$CH_2CH_2CH_2$—, —$C(CH_3)_2$—, and —$CH(CH_3)CH_2$—. Where $R_1$ is —$CH_2$—, the compounds of formula (1) are aryloxy indanamine derivatives; where $R_1$ is —$CH_2CH_2$—, the compounds of formula (1) are aryloxy-1,2,3,4-tetrahydronapthylamine derivatives; where $R_1$ is —$CH_2CH_2CH_2$—, the compounds of formula (1) are aryloxy-5,6,7,8-benzocycloheptenamine derivatives.

The aryloxy moiety of compounds of formula (1) can be mono- or di-substituted at any feasible position(s) in the ring (when q is 1 or 2, respectively) or it can be unsubstituted (when q is 0). X is independently chosen each time it is taken so that when q is 2 the aryloxy moiety is di-substituted with the same or different substituents. Likewise, the fused-ring moiety can be mono- or di-substituted at any of the 4, 5, 6, or 7 position(s) (when p is 1 or 2, respectively) or it can be unsubstituted (when p is 0). Y is independently chosen each time it is taken so that when p is 2 the fused-ring moiety is di-substituted with the same or different substituents. $R_2$ and $R_3$ can be independent moieties or they can be taken together with the nitrogen to which they are attached to form a pyrrolidino, morpholino, piperidino, piperazino, or 4-methylpiperazino group.

As used herein, the term "lower alkyl" refers to an alkyl group comprised of 1 to 6 carbon atoms in straight, branched, or cyclic configuration. The term "lower alkoxy" refers to a lower alkyl group substituted with a single oxygen atom which is attached to the appropriate aryl carbon. The term "halogeno" refers to a fluoro, chloro, bromo or iodo substituent. The term "methylenedioxy" refers to a —O—$CH_2$—O— moiety attached to adjacent aryl carbon atoms. The term "aralkyl" refers to an aromatic ring attached to the nitrogen atom by a $C_1$ to $C_4$ alkylene bridge. For example, the term "aralkyl" includes, but is not limited to benzyl, and the like.

Compounds wherein $R_2$ and/or $R_3$ are $CO_2Me$ or $CO_2Et$, i.e., the methyl or ethyl ester of a carboxy group, are novel intermediates useful in the preparation of compounds of the formula (1). These esters can be made by utilizing procedures analogous to those described below for compounds of the formula (1) and by utilizing standard procedures well known and appreciated in the art.

Compounds of the formula (1) can be employed as free amines or as acid addition salts thereof. The term "acid addition salts" encompasses both organic and inorganic acid addition salts including, for example, those prepared from acids such as hydrochloric, oxalic , and the like. For example, compounds of the formula (1) wherein X or Y is $CF_3$ can be converted to the hydrochloric acid addition salt using conventional methods well known in the art.

As will be recognized and appreciated by those skilled in the art, the compounds of formula (1) can exist in a CIS or TRANS stereoisomeric form with respect to the aryloxy moiety and the amine moiety. It is understood that the present invention encompasses both the CIS or TRANS forms individually and mixtures thereof.

In general, the compounds of formula (1) may be prepared by chemical reactions analogously known in the art, the choice of any specific route of preparation being dependent upon a variety of factors. For example, general availability and cost of the reactants, applicability of certain generalized reactions to specific compounds, and so forth, are all factors which are fully understood by those of ordinary skill in the art and all contribute to the choice of synthesis in the preparation of any specific compound embraced by formula (1). In preparing these compounds, standard procedures and techniques which are well known and appreciated by those of ordinary skill in the art are utilized.

For example, compounds of the formula (1) can conveniently be made according to the general synthetic route outlined in Scheme A.

Scheme A

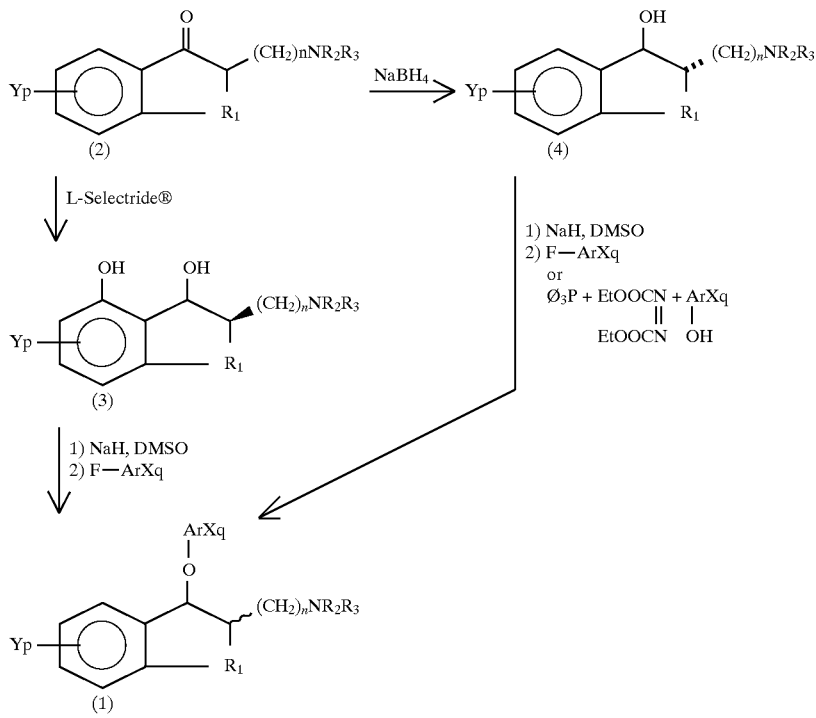

*The Yp, Xq, $R_1$, $R_2$, $R_3$ substituents are as previously defined.

In general, compounds of the formula (1) can be prepared by reacting the appropriately substituted amino ketone (2) with L-Selectride® (lithium tri-O-isobutyl borohydride available from Aldrich) to give the amino alcohol (3). This generally results in the CIS isomer in substantially pure form. The sodium derivative of the amino alcohol (3) which is formed by reacting (3) with sodium hydride (NaH) in dimethylsulfoxide (DMSO) is further reacted with the appropriately substituted aryl fluoride (F-ArXq) in the presence of DMSO to give the corresponding compound of the formula (1). Again this generally results in the CIS isomer in substantially pure form or in a mixture of the CIS and TRANS isomers.

Alternatively, compounds of the formula (1) can be prepared by reacting the appropriately substituted amino ketone (2) with sodium borohydride ($NaBH_4$) which gives the amino alcohol (4) in substantially pure TRANS isomeric form. The compounds of the formula (1) can then be formed by reacting the sodium derivative of the amino alcohol (4) with the appropriately substituted aryl fluoride as described above. In the alternative, the amino alcohol (4) can be reacted with the appropriately substituted aryl alcohol (HO-ArX) in the presence of triphenyl phosphine ($Ø_3P$) and diethoxyazodicarboxylate (EtOOCN=NCOOEt). This procedure can yield compounds of the formula (1) in substantially pure CIS or TRANS forms or in a mixture thereof.

Where it is desired to resolve and isolate the CIS or TRANS stereoisomeric forms of a compound of the formula (1) from a mixture thereof, this resolution can be effected by standard procedures and techniques as are well known and appreciated in the art.

The following examples serve to illustrate synthetic procedures utilized to make compounds of the formula (1) according to the procedure outlined in Scheme A. These examples are intended to be illustrative only and are not intended to limit the invention in any way. All temperatures are in degrees Celsius.

EXAMPLE 1

CIS-2,3-dihydro-1-(2-methoxyphenoxy)-N,N-dimethyl-1H-indene-2-methanamine

STEP A; CIS-2,3-Dihydro-2-(N,N-dimethylaminomethyl)-inden-1-ol

To an ice-cooled suspension of 2.25 g (0.01M) of 2,3-dihydro-2-(N,N-dimethylaminomethyl)-1H-inden-1-one hydrochloride in 50 ml of dry tetrahydrofuran was added 25 ml of a 1M solution of L-Selectride®. The mixture was stirred for 1.5 hours and decomposed with 5 ml of 10% sodium hydroxide solution. The solvent was evaporated at reduced pressure and the residue distributed between ether and water. The ether layer was separated and extracted with dilute hydrochloric acid. Basification of the acid extract gave an oil which was extracted into ethyl acetate. Evaporation and Kugelrohr distillation at 90°–100°/0.4 mm gave 0.92 g (48%) of amino alcohol.

Anal. Calcd for $C_{12}H_{17}NO$ C=75.35; H=8.96,; N=7.32 Fd: C=74.86; H=9.00; N=7.25

By procedures analogous to that described above, the following amino alcohols can be prepared:

CIS-2,3-dihydro-2-(N-methyl-N-phenylmethylamino) methyl-1H-inden-1-ol Bp 135°–140°/0.3 mm Anal. Calcd for $C_{18}H_{21}NO$ C=80.86; H-7.92; N-5.24 Fd: C=80.68; H=7.95; N=5.21

CIS-6-chloro-2,3-dihydro-2-(N,N-dimethylamino)methyl-1H-inden-1-ol Bp 118°–121°/0.3 mm Anal. Calcd for $C_{12}H_{16}ClNO$ C=63.85; H=7.15; N=6.21 Fd: C=63.80; H=7.30; N=6.31

CIS-2,3-dihydro-2-(4-morpholino)methyl-1H-inden-1-ol Bp 119°–127°/0.3 mm

Anal. Calcd. for $C_{14}H_{19}NO_2$ C=72.07; H=8.21; N=6.00 Fd: C=71.81; H=8.15; N=5.77
TRANS-2-dimethylaminomethyl-1,2,3,4-tetrahydronaphthalen-1-ol Bp 127°–35°/0.4 mm
Anal. Calcd for $C_{13}H_{19}NO$ C=76.05; H=9.33; N=6.82 Fd: C=75.83; H=9.21; N=6.50
TRANS-2,3-dihydro-2-dimethylaminomethyl-inden-1-ol m.p. 65°–67°
Anal. Calcd. for $C_{12}H_{17}NO$ C=75.35; H=8.96; N=7.32 Fd: C=75.32; N=8.96; N=7.26
TRANS-2,3-dihydro-6-fluoro-2-dimethylaminomethylinden-1-ol m.p. 93°–95°
Anal. Calcd. for $C_{12}H_{16}FNO$ C=68.87; H=7.71; N=6.69 Fd: C=69.02; H=7.84; N=6.57
CIS-2,3-dihydro-6-methoxy-2-dimethylaminomethylinden-1-ol Bp 102°–110°/0.3 m
Anal. Calcd for $C_{13}H_{15}NO_2$ C=70.55; H-8.66; N=6.33 Fd: C=70.23; H=8.86; N=6.20
CIS-2,3-dihydro-6-fluoro-2-dimethylaminomethylinden-1-ol Bp 90°–93°/0.3 m
Anal. Calcd. for $C_{12}H_{16}FNO$ C=68.87; H=7.71; N=6.60 Fd: C=68.82; H=7.82; N=6.52
CIS-2,3-dihydro-5-fluoro-2-(N,N-diethylamino)methyl-1H-inden-1-ol
CIS-2,3-dihydro-3,3-dimethyl-2-(N,N-dimethylamino)methyl-6-methoxy-1H-inden-1-ol
CIS-2,3-dihydro-2-(N-ethyl-N-methylamino)methyl)-5,6-dimethoxy-1H-inden-1-ol
CIS-6-(N,N-dimethylamino)methyl-5,6,7,8-tetrahydro-benzocycloheptene-5-ol
CIS-2,3-dihydro-6-fluoro-2-(4-methylpiperazino)methyl-1H-inden-1-ol
CIS-2,3-dihydro-2-(1-pyrolidino)-1H-inden-1-ol
CIS-2,3-dihydro-2-(N,N-dimethylamino)ethyl-1H-inden-1-ol
CIS-2-diethylamino-1,2,3,4-tetrahydronaphthalene-1-ol
CIS-2-(dimethylamino)methyl-1,2,3,4-tetrahydronaphthalen-1-ol
STEP B: CIS-2,3-dihydro-1-(2-methoxyphenoxy)-N,N-dimethyl-1H-indene-2-methanamine A mixture of 0.75 g of 50% sodium hydride dispersion in oil and 10 ml of dimethylsulfoxide was heated in an oil bath at 65° in a nitrogen atmosphere for 30 minutes and cooled to room temperature. CIS-2,3-dihydro-2-(N,N-dimethylaminomethyl)-inden-1-ol (1.91 g, 0.01M) was added and the mixture stirred for 15 minutes. 2-Fluoroanisole (3.5 ml) was added and the mixture heated at 90° overnight. After cooling and diluting with water, the product was extracted into ethyl acetate. The amine was isolated by chromatography on silica and elution with 10% ethyl acetate in hexane. Kugelrohr distillation at 123°–125°/0.4 mm gave the pure amine.
Anal. Calcd. for $C_{19}H_{23}NO_2$ C=76.73; H-7.80; N-4.71 Fd: C=76.62; H=7.99; N=4.98
By procedures analogous to that described above, the following compounds of the formula (1) can be prepared:
CIS-2,3-dibydro-N-methyl-N-(phenylmethyl)-1-(4-trifluoro-methylphenoxy)-1H-indene-2-methanamine hydrochloride mp 218°
Anal. Calcd. for $C_{25}H_{24}F_3NO.HCl$ C=67.03; H=5.63; N=3.13 Fd: C=67.16; H=5.57; N=3.16
CIS-2,3-dihydro-N,N-dimethyl-1-phenoxy-1H-indene-2-methanamine Bp 110°–115°/0.3 mm
Anal. Calcd for $C_{18}H_{21}NO$ C=80.86; H=7.92; N=5.24 Fd: C=80.58; H=7.93; N=5.01
CIS-2,3-dihydro-N,N-dimethyl-1-(4-trifluoromethylphenoxy)-1H-indene-2-methanamine hydrochloride mp 178°–180°
Anal. Calcd for $C_{19}H_{20}F_3NO.HCl$ C=61.37; H=5.69; N=3.77 Fd: C=61.23; H=5.79; N=3.70
CIS-1,2,3,4-tetrahydro-1-(2-methoxyphenoxy)-N,N-dimethyl-2-naphthalenemethanamine Bp 135°–140°/0.4 mm
Anal. Calcd for $C_{20}H_{25}NO_2$ C=77.13; H=8.09; N-4.50 Fd: C=77.02; H=8.05; N=4.52
CIS-4-{[2,3-dihydro-1-(2-methoxyphenoxy)-1H-inden-2-yl]methyl}morpholine oxalate mp 144°–145°
Anal. Calcd. for $C_{21}H_{25}NO_3.C_2H_2O_4$ C=64.32; H=6.34; N-3.26 Fd: C=64.08; H=6.47; N=3.19
CIS-1-(3,4-dichlorophenoxy)-2,3-dihydro-N,N-dimethyl-1H-indene-2-methanamine hydrochloride mp 192°–193°
Anal. Calcd for $C_{18}H_{19}Cl_2NO.HCl$ C=58.00; H=5.41; N-3.76 Fd: C=58.11; H=5.49; N=3.68
CIS-6-chloro-2,3-dihydro-1-(2-methoxyphenoxy)-N,N-dimethyl-1H-indene-2-methanamine maleate mp 141°–143°
Anal. Calcd. for $C_{19}H_{22}ClNO_2.C_4H_4O_4$ C=61.67; H=5.85; N=3.13 Fd: C=61.39; H=5.97; N=3.01
CIS-2,3-dihydro-N,N-dimethyl-1-(2-methylphenoxy)-1H-indene-2-methanamine oxalate
CIS-2,3-dihydro-N,N-dimethyl-1-phenoxy-1H-indene-2-amine
CIS-2,3-dihydro-1-(3,4-dimethoxyphenoxy)-N,N-dimethyl-1H-indene-2-methanamine
CIS-5-(4-fluorophenoxy)-5,6,7,8-tetrahydrobenzocyclohepten-6-methanamine
CIS-1-(3-chlorophenoxy)-2,3-dihydro-3,3, N,N-tetramethyl-6-methoxy-1H-indene-2-methanamine

EXAMPLE 2

CIS and TRANS-1,2,3,4-tetrahydro-1-(2-methoxyphenoxy)-N,N-dimethyl-2-naphthalenemethanamine A mixture of 8.21 g (0.04M) of TRANS-1,2,3,4-tetrahydro-2-(N,N-dimethylaminomethyl)naphthalen-1-ol, 11.54 g (0.044M) of triphenyl phosphine, 5.46 g (0.044M) of 2-methoxyphenol and 100 ml of benzene was stirred and a solution of 7.83 g (0.004M) of 95% diethyl azodicatrboxylate in 25 ml of benzene was added dropwise over 45 minutes. After 2 hours, the mixture was filtered and extracted with cold 3% hydrochloric acid. The acid extracts were made basic with dilute sodium hydroxide and the oil which separated was extracted into ether. The solvent was removed and the residual oil chromatographed on silica gel. Elution with 1:1 ether-chloroform gave the TRANS-isomer-1.20 g, Bp 135°–38°/0.4 mm.
Anal. Calcd for $C_{20}H_{25}NO_2$: C=77.13; H=8.09; N-4.50 Fd: C=77.15; H=8.21; N=4.56
Elution with ether gave the CIS-isomer, 2.64 g. Bp 135°–40°/0.4 mm
Anal. Calcd for $C_{20}H_{25}NO_2$: C=77.13; H=8.09; N=4.50 Fd: C=77.02; H=8.05; N=4.52.

EXAMPLE 3

CIS and TRANS-2,3-dihydro-1-(2-methoxyphenoxy)-N,N-dimethyl-1H-inden-2-amine oxalate A mixture of 1.0 g sodium hydride (50% suspension in oil) and 25 ml of dimethylsulfoxide was heated in an oil bath at 60° for 0.5 hours. The mixture was cooled and 2.22 g (0.013 m) of CIS-2,3-dihydro-2-N,N-dimethylamino-1H-inden-1-ol was added. After stirring 10 minutes, 3.3 g (0.026M) of 2-fluoroanisol was added and the mixture heated at 90° for 21 hours. After cooling, the mixture was poured into water and extracted with ethyl acetate. Evaporation left an oil which was chromatographed on silica gel. Elution with ethyl acetate gave the TRANS-isomer which was converted into the oxalate salt in ether (0.72 g, m.p. 172°73°).

Anal. Calcd. for $C_{18}H_{21}NO_2.C_2H_2O_4$ C=64.33; H-6.21; N=3.75 Fd: C=64.23; H=6.29; N=3.72

The CIS isomer was eluted with 9:1 ethyl acetate-methanol and converted to the oxalate salt in ether—0.92 g, m.p. 149°–50° Fd: C=64.16; H=6.27; N=3.80

The starting materials for the above reaction scheme, i.e., the appropriately substituted amino ketones (2) and aryl fluoride/alcohols, are readily obtained through the use of commonly available reagents modified if required through standard synthetic schemes, procedures and techniques as are well known and appreciated by those of ordinary skill in the art.

For example, the appropriate amino alcohol intermediate for compounds of the formula (1) wherein n is 0 can be prepared by procedures analogous to that described by Huebner, et al, [J. Org. Chem. 35, 1149 (1970)].

The appropriate amino ketone starting material for compounds of the formula (1) wherein n is 0, 1 or 2 can be prepared by procedures analogous to that described in U.S. Pat. No. 2,947,756.

In another embodiment, the present invention provides a method of treating depression in a patient in need thereof comprising administering a therapeutically effective antidepressant amount of one or more compounds of the formula (1). In addition, the present invention provides methods of inhibiting synaptic norepinephrine uptake, or of inhibiting synaptic serotonin uptake, or of inhibiting both synaptic norepinephrine and serotonin uptake in a patient in need thereof comprising administering a therapeutically effective inhibitory amount of one or more compounds of the formula (1).

It is generally accepted by those skilled in the art that compounds such as desipramine, which inhibit synaptic norepinephrine uptake, and compounds such as fluoxetine, which inhibit synaptic serotonin (5-hydroxytryptamine or 5-HT) uptake provide antidepresssant effects upon administration to patients suffering from depression.

As used herein, the term "patient" refers to a warm-blooded animal, such as a mammal, which is suffering from depression. It is understood that dogs, cats, rats, mice, horses, bovine cattle, sheep, and humans are examples of animals within the scope of the meaning of the term.

The term "depression" refers to a disease or an abnormal state or condition characterized clinically by a psychiatric syndrome comprising, for example, a dejected mood, psychomotor retardation, insomnia, weight loss, and the like. Depression is readily diagnosed by a clinical diagnostician using practices and procedures well known and appreciated by those of ordinary skill in the art.

It is believed that there is a general correlation between compounds which have a biological effect of inhibiting synaptic norepinephrine or serotonin uptake and the medical effect of being useful in treating depression in a patient suffering therefrom. As used herein, the term "treating depression" refers to providing an antidepressant effect by relieving one or more clinical signs and symptoms of depression in a patient suffering therefrom.

The present invention provides compounds which inhibit both synaptic norepinephrine and serotonin uptake and are therefore believed to be useful in treating depression by administration to a patient suffering therefrom. Although the compounds of the formula (1) inhibit both synaptic norepinephrine and serotonin uptake, in any individual compound these inhibitory effects may be manifested at the same or vastly different concentrations or doses. As a result, some compounds of the formula (1) are useful in treating depression at doses at which synaptic norepinephrine uptake may be substantially inhibited but at which synaptic serotonin uptake is not substantially inhibited. And, conversely, some compounds of the formula (1) are useful in treating depression at doses at which synaptic serotonin uptake may be substantially inhibited but at which synaptic norepinephrine uptake is not substantially inhibited. Other compounds of formula (1) are useful in treating depression at doses at which both synaptic norepinephrine and serotonin uptake are substantially inhibited.

The concentrations or doses at which a test compound inhibits synaptic norepinephrine and serotonin uptake is readily determined by the use of standard assay and techniques well known and appreciated by one of ordinary skill in the art. For example, the degree of inhibition at a particular dose in rats can be determined by the method of Dudley, et al., [J. Pharmacol. Exp. Ther. 217, 834–840 (1981)].

The therapeutically effective inhibitory dose is one which is effective in substantially inhibiting synaptic norepinephrine uptake or synaptic serotonin uptake or both synaptic norepinephrine and serotonin uptake. The therapeutically effective inhibitory dose can be readily determined by those skilled in the art by using conventional range finding techniques and analagous results obtained in the test systems described above. The therapeutically effective inhibitory dose will generally be the same as the therapeutically effective antidepressant dose.

A therapeutically effective antidepressant or inhibitory dose can be readily determined by the attending diagnostician, as one skilled in the art, by the use of conventional techniques and by observing results obtained under analogous circumstances. In determining the therapeutically effective dose, a number of factors are considered by the attending diagnostician, including but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

In treating depression or in inhibiting synaptic norepinephrine and/or serotonin uptake, a compound of formula (1) can be administered in any manner which makes the compound bioavailable in effective amounts, including oral and parenteral routes. For example, compounds of the formula (1) can be administered orally, subcutaneously, intramuscularly, intravenously, TRANSdermally, intranasally, rectally, and the like. Oral administration is generally preferred.

A therapeutically effective antidepressant or inhibitory amount of a compound of the formula (1) is expected to vary from about 0.1 milligrams per kilogram of body weight per day (mg/kg/day) to about 100 mg/kg/day. Preferred amounts are expected to vary from about 1 to about 10 mg/kg/day.

The compounds of this invention can be administered in various forms to achieve the desired effect. The compounds which generally are free amines in liquid form can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may also be formulated and administered in the form of their acid addition salts for purposes of stability, convenience of crystallization, increased solubility and the like where these salts are pharmaceutically acceptable.

In another embodiment, the present invention provides a pharmaceutical composition comprising a therapeutically effective amount of a compound of the formula (1) in admixture or otherwise in association with one or more pharmaceutically acceptable carriers or excipients. The term "therapeutically effective amount" refers to therapeutically effective antidepressant or inhibitory amount as appropriate.

The pharmaceutical compositions are prepared in a manner well known perse in the pharmaceutical art. The carrier or excipient may be solid, semi-solid, or liquid material which can serve as a vehicle or medium for the active ingredient. Suitable carriers or excipients are well known in the art perse. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants; binders such as microcrystalline cellulose, gum tragacanth or gelatin; excipients such as starch or lactose, disintegrating agents such as alginic acid, Primogel, cornstarch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of the formula (1) in their end-use application.

Compounds of the formula (1) which function as essentially equipotent inhibitors of synaptic norepinephrine and serotonin uptake are generally preferred. Essentially equipotent inhibitors are those which inhibit synaptic norepinephrine and serotonin uptake at substantially the same concentrations or at substantially the same doses (i.e., the therapeutically effective inhibitory dose for synaptic norepinephrine uptake and for synaptic serotonin uptake are substantially equivalent).

Furthermore, compounds of the formula (1) wherein $R_2$ is methyl and $R_3$ is hydroxy and those wherein $R_2$ and $R_3$ are each methyl are preferred. Compounds wherein n is 1 are generally preferred. Compounds wherein $R_1$ is —$CH_2$— or —$CH_2CH_2$— are preferred. Compounds wherein p and q are O are also generally preferred. For compounds wherein p is 1, chloro is preferred for Y. For compounds wherein q is 1, $CF_3$, methoxy and chloro are preferred for X.

The following compounds are particularly preferred embodiments of the present invention:

2,3-dihydro-1-(2-methoxyphenoxy)-N,N-dimethyl-1H-indene-2-methanamine, 2,3-dihydro-N-methyl-2-[4-(trifluoromethyl)phenoxy]-1H-indene-2-methanamine hydrochloride.

As a further embodiment of the present invention, an improvement is provided in the method of treating depression in a patient in need thereof. This improvement comprises inhibiting both synaptic norepinephrine uptake and synaptic serotonin uptake in the depressed patient. This improved treatment can be effected by administering a therapeutically effective inhibitory amount of a compound which functions as both a synaptic norepinephrine and serotonin uptake inhibitor or by conjunctive therapy with therapeutically effective inhibitory amounts of (a) a compound which functions as a synaptic norepinephrine uptake inhibitor, and (b) a compound which functions as a synaptic serotonin uptake inhibitor.

As indicated above, it is generally believed that there is a correlation between compounds which have a biological effect of inhibiting synaptic norepinephrine uptake such as desipramine, or synaptic serotonin uptake, such as fluoxetine, and the medical effect of being useful in treating depression in a patient suffering therefrom. This inhibition of norepinephrine or serotonin uptake in the synaptic gap is believed to effect a down-regulation of β-adrenergic receptors which correlates well with the onset of clinical effectiveness of compounds which are useful in treating depression. Surprisingly, applicants now have found that inhibition of both synaptic norepinephrine and serotonin uptake in a patient suffering from depression has a synergistic beneficial effect in effecting a down-regulation of β-adrenergic receptors and therefore believe that this treatment will provide a significant improvement in the treatment of depression.

The number of β-adrenergic receptors in rat cerebral cortical membranes was measured after a 4 day and 14 day course of one of the following treatments:

a) saline control (intraperitoneal injection—i.p.)

b) desipramine (5 mg/kg/day, i.p.)

c) fluoxetine (10 mg/kg/day, i.p.) or (10 mg/kg bid, i.p.)

d) desipramine (5 mg/kg/day, i.p.) and fluoxetine (10 mg/kg/day, i.p.) or (10 mg/kg bid, i.p.)

Male Sprague-Dawley rats (175–200 g) were assigned randomly to one of the four treatment groups above and were treated as indicated for either 4 or 14 days. The animals were sacrificed 24 hours after their last treatment and cerebral cortical membranes were isolated. These membranes were assayed for β-adrenergic receptor number by the method of Bylund and Snyder [Mol. Pharmacol. 12, 568 (1976)] by measuring the amount of [$^3$H]dihydro-alprenolol ([$^3$H]-DHA) bound. The results as shown in Table 1 indicate that combined treatment with desipramine and fluoxetine results in a substantially greater down-regulation of β-adrenergic receptors than treatment with either desipramine or fluoxetine alone. Furthermore, the combined treatment results in a synergistic effect in providing a down-regulation which is substantially greater than what would have been expected if desipramine and fluoxetine produced merely additive effects on β-adrenergic receptor down-regulation.

Compounds which function as synaptic norepinephrine uptake inhibitors and/or synaptic serotonin uptake inhibitors are readily identified by standard techniques and procedures well known and appreciated by those skilled in the art, such as, for example, the method described by Dudley, et al. [J. Pharmacol. Exp. Ther. 217, 834 (1981)]. Therapeutically effective inhibitory amounts of these

TABLE 1

The Effect of the Combined Treatment with Desipramine and Fluoxetine on Rat Cortical β-Receptors

| Treatment | | [$^3$H]-DHA Specifically Bound (fmol/mg protein) | % Control |
|---|---|---|---|
| A) | Saline | 41.8 ± 1.4 | — |
| | Desipramine | 35.9 ± 1.2* | 86 |
| | Fluoxetine | 37.9 ± 1.8 | 91 |
| | Desipramine + Fluoxetine | 26.5 ± 1.2*+ | 64 |
| B) | Saline | 54.6 ± 3.1 | — |
| | Desipramine | 49.2 ± 2.4 | 90 |

TABLE 1-continued

The Effect of the Combined Treatment with Desipramine and Fluoxetine on Rat Cortical β-Receptors

| Treatment | [$^3$H]-DHA Specifically Bound (fmol/mg protein) | % Control |
|---|---|---|
| Fluoxetine | 51.8 ± 1.7 | 95 |
| Desipramine + Fluoxetine | 40.0 ± 0.9* | 73 |

A) Desipramine (5 mg/kg, i.p.) and Fluoxetine (10 mg/kg, i.p.) were administered as indicated for 14 days. Six animals per group. Values are mean ± SEM.
B) Desipramine (5 mg/kg, i.p.) and Fluoxetine (10 mg/kg bid, i.p.) were administered as indicated for 4 days. Six animals per group. Values are mean ± SEM.
*p < 0.05 vs saline
+P < 0.05 vs Desipramine compounds can be determined as described above. As used herein, the term "conjunctive therapy" refers to coadministration of a compound which functions as synaptic norepinephrine uptake inhibitor along with a compound which functions as a synaptic serotonin uptake inhibitor at essentially the same time.

The following are examples of synaptic serotonin uptake inhibitors which can be used according to the present invention in conjunctive therapy with a synaptic norepinephrine uptake inhibitor: fluoxetine, tomoxetine, citalopram, zimelidine, piroxitine, trazodone and the like. The following are examples of synaptic norepinephrine uptake inhibitors which can be used according to the present invention in conjunctive therapy with a synaptic serotonin uptake inhibitor: desipramine, nartryptaline and the like.

Of course, certain compounds, such as those of the present invention, function as both synaptic norepinephrine uptake inhibitors and synaptic serotonin uptake inhibitors. Administration of such compounds which function as inhibitors of synaptic norepinephrine and serotonin uptake is also understood to be within the scope of the present invention. Administration of compounds which function as essentially equipotent inhibitors of synaptic norepinephrine and serotonin uptake is preferred.

In effecting this improvement in the treatment of depression, one or more compounds which function as synaptic norepinephrine and synaptic serotonin uptake inhibitors may be administered to a patient in the same manner as described above for the compounds of this invention.

I claim:

1. A method of treating depression in a patient in need thereof which comprises inhibiting synaptic serotonin and norepinephrine uptake by conjunctive therapy with therapeutically effective inhibitory amounts of (1) the serotonin uptake inhibitor fluoxetins and (2) the norepinephrine uptake inhibitor desipramine.

* * * * *